US007122383B2

(12) United States Patent
Jones et al.

(10) Patent No.: US 7,122,383 B2
(45) Date of Patent: *Oct. 17, 2006

(54) FLUORESCENT POLYMER SUPERQUENCHING-BASED BIOASSAYS

(75) Inventors: Robert M. Jones, Albuquerque, NM (US); Sriram Kumaraswamy, Santa Fe, NM (US); Liangde Lu, Mesa, AZ (US); Frauke Rininsland, Santa Fe, NM (US); Kevin Ley, Santa Fe, NM (US); Wensheng Xia, Santa Fe, NM (US); Duncan McBranch, Santa Fe, NM (US); David G. Whitten, Santa Fe, NM (US)

(73) Assignee: QTL Biosystems, LLC, Santa Fe, NM (US)

( * ) Notice: Subject to any disclaimer, the term of this patent is extended or adjusted under 35 U.S.C. 154(b) by 509 days.

This patent is subject to a terminal disclaimer.

(21) Appl. No.: 10/098,387

(22) Filed: Mar. 18, 2002

(65) Prior Publication Data

US 2002/0150759 A1    Oct. 17, 2002

Related U.S. Application Data

(60) Provisional application No. 60/276,090, filed on Mar. 16, 2001, provisional application No. 60/314,101, filed on Aug. 23, 2001.

(51) Int. Cl.
*G01N 33/543* (2006.01)

(52) U.S. Cl. .......................... 436/518; 435/6; 435/7.1; 435/7.72; 435/91.1; 436/172; 436/501; 436/94; 536/23.1

(58) Field of Classification Search ................ 435/6, 435/29, 7.72, 91.1, 7.1; 436/172, 501, 94; 536/23.1
See application file for complete search history.

(56) References Cited

U.S. PATENT DOCUMENTS 4,863,876 A * 9/1989 Hevey ........................ 436/537

(Continued)

FOREIGN PATENT DOCUMENTS

WO          WO 99/37814          7/1999

(Continued)

OTHER PUBLICATIONS

Edward T. Maggio (Enzyme—Immunoassay, Library of Congress Card No. 79-25070).*

(Continued)

*Primary Examiner*—Long V. Le
*Assistant Examiner*—Deborah A. Davis
(74) *Attorney, Agent, or Firm*—DLA Piper US LLP

(57) ABSTRACT

A chemical composition including a fluorescent polymer and a receptor that is specific for both a target biological agent and a chemical moiety including (a) a recognition element, (b) a tethering element, and (c) a property-altering element is disclosed. Both the fluorescent polymer and the receptor are co-located on a support. When the chemical moiety is bound to the receptor, the property-altering element is sufficiently close to the fluorescent polymer to alter the fluorescence emitted by the polymer. When an analyte sample is introduced, the target biological agent, if present, binds to the receptor, thereby displacing the chemical moiety from the receptor, resulting in an increase of detected fluorescence. Assays for detecting the presence of a target biological agent are also disclosed.

20 Claims, 17 Drawing Sheets

U.S. PATENT DOCUMENTS

| | | | |
|---|---|---|---|
| 4,950,587 A | | 8/1990 | Roberts et al. |
| 5,356,785 A | * | 10/1994 | McMahon et al. ......... 435/7.92 |
| 5,612,221 A | | 3/1997 | Simons et al. |
| 5,928,869 A | * | 7/1999 | Nadeau et al. ................. 435/6 |
| 5,928,888 A | * | 7/1999 | Whitney ...................... 435/29 |
| 5,968,762 A | | 10/1999 | Jadamec et al. |
| 6,013,531 A | | 1/2000 | Wang et al. |
| 6,403,311 B1 | | 6/2002 | Chan |

FOREIGN PATENT DOCUMENTS

| | | |
|---|---|---|
| WO | WO 00/42222 | 7/2000 |
| WO | WO 00/66790 | 11/2000 |
| WO | WO0066790 | 11/2000 |
| WO | WO 01/63282 | 8/2001 |
| WO | WO 01/85997 | 11/2001 |

OTHER PUBLICATIONS

Chen, L., et al., "Highly Sensitive Biological and Chemical Sensors Based on Reversible Fluorescence Quenching in a Conjugated Polymer", PNAS, vol. 96, No. 22, 12287-12292 (1999).

Jones, et al., "Building highly sensitive dye assemblies for biosensing from molecular building blocks", Proceedings of the National Academy of Sciences of the United States of America, vol. 98, No. 26, pp. 14769-14772, (2001).

Jones, et al., "Tuning of Superquenching in Layered and Mixed Fluorescent Polyelectrolytes", Journal of the American Chemical Society, vol. 123, No. 27, pp. 6726-6727, (2001).

* cited by examiner

16 (R1 CH3, R2 N-C8H17, R3 CH3, R4 -(CH2)3-COOH)

17 DH (R1 R2 N-C8H17, R3 CH3, R4 -(CH2)3-COOH)

18 (R1 R2 N-C4H9, R3 CH3, R4 -(CH2)3-COOH)

19 (R1 R2 N-C4H9, R3 CH3, R4 -(CH2)7-COOH)

20 (R1 R2 N-C8H17, R3 R4 -(CH2)3COOH)

21

22

23:QTL (NONFLUORESCENT)  23:L (OR L') (FLUORESCENT)

Bead, Nanoparticle, Surface

1. Covalently tether fluorescent polymer or oligomer

2. Covalently tether Streptavidin, Avidin or receptor to surface

FLUORESCENT POLYMER SUPERQUENCHING-BASED BIOASSAYS

This application claims priority from U.S. Provisional Application Ser. No. 60/276,090 filed Mar. 16, 2001 and U.S. Provisional Application Ser. No. 60/314,101 filed Aug. 23, 2001. The entirety of those provisional applications is incorporated herein by reference.

BACKGROUND OF THE INVENTION

1. Field of the Invention

The present invention relates to a fluorescent biosensor that functions by a novel Quencher-Tether-Ligand (QTL) mechanism. In particular, the present invention relates to improving the polymer-QTL approach by co-locating the fluorescent polymer (or polymer ensemble, including self-assembled polymers) and a receptor for the QTL bioconjugate and target analyte on the same solid support.

2. Discussion of the Background

The polymer-QTL (Quencher-Tether-Ligand) approach is a single-step, instantaneous, homogeneous assay where the amplification step is intrinsic to the fluorescent polymer. The polymer-QTL approach provides a system for effective sensing of biological agents by observing fluorescence changes. The key scientific basis is the amplification of quenching of fluorescence that can be obtained with certain charged conjugated polymers and small molecule quenchers. In addition, the process is uniquely simple because there are no reagents.

In the "biosensor" mode, the QTL approach functions by having a fluorescent polymer quenched by a specially constructed "quencher-tether-ligand" (QTL) unit as shown in the diagram set forth in FIG. 1. Addition of an analyte containing a biological receptor specific to the ligand is expected to remove the QTL conjugate from the polymer which results in a "turning on" of the polymer fluorescence. A fluorescent polyelectrolyte-based superquenching assay has been shown to offer several advantages over conventional small molecule based fluorescence assays. For example, conjugated polyelectrolytes, dye-pendant polyelectrolytes, etc. can "harvest" light effectively both by absorption and by superquenching (1–5). The enhanced absorbing power of the polymers is indicated by the observation that even sub nanomolar solutions of some of these materials are visibly colored. The fluorescence of these polymers can be detected at even lower concentrations. Superquenching occurs in the presence of small molecules capable of serving as electron transfer or energy transfer quenchers to the polymer or one of its repeat units.

The "Stern-Volmer" quenching constants ($K_{SV}$) for these polymers have been shown to be as high as $10^8$–$10^9$ $M^{-1}$, and it is anticipated that values as high as $10^{11}$ $M^{-1}$ may be attainable (6). Such high values for $K_{SV}$ toward quenchers oppositely charged to the polyelectrolyte are initiated by strong nonspecific binding between the quencher and the polyelectrolyte. Subsequent amplified quenching occurs due to a combination of excitonic delocalization and energy migration to the "trapsite" where the quencher is in close proximity with the polymer.

It has also been shown that enhanced superquenching may be obtained when the polymers are adsorbed onto charged supports including surfaces, polymer microspheres, and inorganic nanoparticles (7,8). Superquenching has also been observed in the same supported formats for monomers or small oligomers self-assembled into "virtual" polymers. Polymer (and "virtual" polymer) superquenching has been adapted to biosensing by constructing QTL conjugates containing a potential superquenching component (Q) tethered (T) to a bioreceptor (L) or ligand for a specific biomolecule (1).

A fluorescence based assay is realized when the QTL conjugate is used to quench the polymer either in solution or in supported formats at solution-solid or solution-particle interfaces (1,7,8). For example, fluorescent polyelectrolytes, including conjugated and J-aggregate polymers, can be used for sensitive biodetection and bioassays in solution formats. The basis of this detection is the combination of the "superquenching" sensitivity of these molecules to quenchers of opposite or neutral charges with the synthesis of a quencher-recognition conjugate (e.g., a QTL molecule). In the original formulation, the QTL conjugate quenches the polymer ensemble by nonspecific binding. Addition of a target bioagent capable of binding with the L component of the QTL conjugate results in a removal of the QTL conjugate from the polymer and a turning on of the polymer fluorescence.

A fluorescence turn off (or modulation) assay has also been developed based on polymer superquenching (5). In this case, the target molecule is a bioagent L, or L', corresponding to the L component of the QTL conjugate, and the receptor is a biomolecule that strongly associates with L, L' or the QTL conjugate. One example is a direct competition assay in which L (or L') in unknown amount is allowed to compete with the QTL conjugate for the binding sites of a measured amount of the receptor. The polymer fluorescence is quenched by non-bound QTL to an extent depending on the amount of L (or L') present. In another example, the QTL conjugate is preassociated with the receptor; when all of the QTL conjugates are associated with the receptor sites, no quenching is observed. Addition of L (or L') to the sample results in the release of the QTL conjugate with concomitant quenching of the polymer fluorescence.

All of the above assay formats depend on nonspecific quenching of the polymer fluorescence by association of the QTL conjugate with the polymer. A complication with these assays is the competing nonspecific interactions of other components of the assay sample with either the polymer, the QTL conjugate, or both, which result in a modulation of the quenching. In the present invention, modifications of the polymer superquenching allow the construction of improved assays which overcome these effects and provide for a more versatile and robust sensor.

SUMMARY OF THE INVENTION

It is an object of the invention to provide a novel chemical moiety formed of a quencher (Q), a tether (T), and a ligand (L) specific for a particular bioagent.

It is another object of the invention to provide an assay to detect a target agent in a sample using the novel QTL molecule of the present invention and a fluorescent polymer.

It is yet another object of the invention to rapidly and accurately detect target biological agents in a sample.

It is a feature of the invention that the fluorescent polymer and the receptor for the target biological agent are co-located on a support.

It is another feature of the invention that the co-located fluorescent polymer and the receptor are tethered to the support.

It is yet another feature of the invention that the co-located fluorescent polymer and receptor are covalently linked to the support.

It is also a feature of the present invention to covalently link the receptor to the fluorescent polymer.

It is a further feature that the change in fluorescence is indicative of the presence of the target biological agent.

It is another feature of the invention that the quench event is a result of a specific interaction between the receptor and the QTL conjugate.

It is yet another feature of the present invention that the assembled monomers behave like polymers.

It is an advantage of the invention that the assays of the present invention can be carried out in operationally different formats.

A further advantage of the invention is the versatility provided by the ability to control the co-located assembly of a specific polymer ensemble-receptor either spatially as on a rigid support or on different particles.

It is another advantage of the present invention that assays according to the present invention are both homogeneous and near instantaneous.

It is yet another advantage of the invention that the ability to control the co-located polymer assembly either spatially (e.g., on a rigid support) or on different particles offers great versatility.

It is a further advantage that superquenching occurs due to specific ligand-receptor interactions.

DESCRIPTION OF THE PREFERRED EMBODIMENTS

Figure 1:
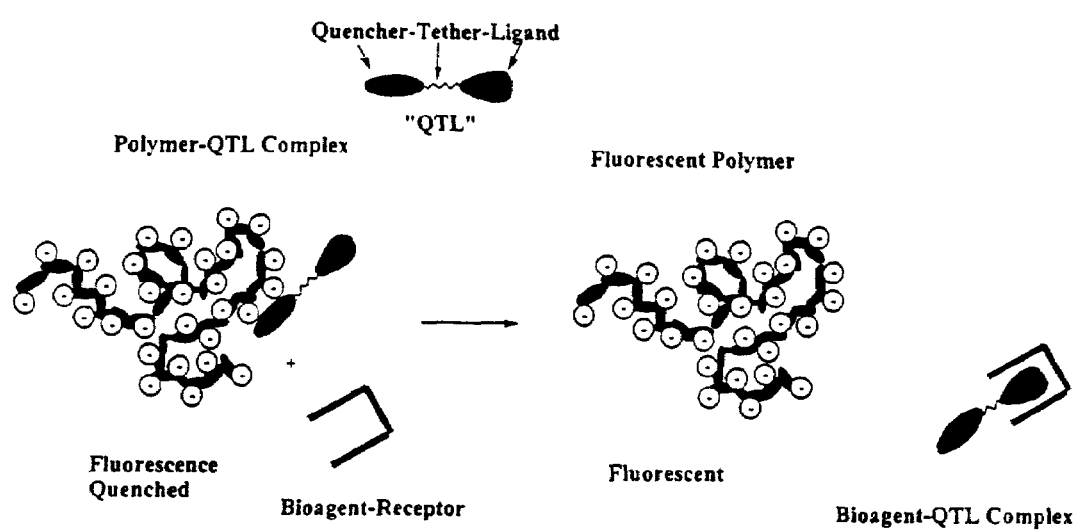
FIG. 1 is a general illustration of the QTL approach.

A key scientific basis for the polymer QTL approach is the amplification of quenching of fluorescence (superquenching) that may be obtained with certain polymers (including, but not limited to, charged polymers, conjugated polymers and dye-pendant polyelectrolytes in which the chromophores are collected by non-covalent interactions (e.g., J-aggregation)) and small molecule quenchers. The fluorescent polymers provide amplification over conventional molecular fluorophores both by virtue of their light-harvesting properties (collective excitation) and their sensitivity to superquenching (i.e., one quencher may extinguish luminescence from an entire polymer chain or a collection of polymers, oligomers, or monomers). In some cases, enhanced quenching may be observed when mixtures of polymers are used or when the polymers are adsorbed or otherwise assembled onto surfaces. The same enhancement of quenching can be observed when monomers or oligomers of some of the chromophore repeat units are assembled either by covalent attachment or adsorption onto a support. The support may be, but is not limited to, any of the following: polymer or silica microspheres, organic or inorganic nanoparticles, magnetic beads or particles, semiconductor nanocrystals, tagged or luminescent particles, membranes and planar or corrugated solid surfaces.

Fluorescent polymer superquenching has been adapted to biosensing applications through the use of "QTL" bioconjugates (1, 4–6, 8). The QTL approach to biosensing takes advantage of the superquenching of fluorescent polyelectrolytes by electron transfer and energy transfer quenchers. In its simplest approaches, the fluorescent polymer, P, forms an association complex with a QTL bioconjugate, usually one with the opposite charge of P. QTL bioconjugates include a small molecule electron transfer or energy transfer quencher (Q), linked through a covalent tether to a ligand, L, that is specific for a particular bioagent or receptor. The binding of the QTL bioconjugate by the bioagent either removes the QTL bioconjugate from the fluorescent polymer, or modifies its quenching efficiency, thus allowing sensing of the bioagent in a readily detectable way.

Suitable examples of ligands that can be used in "QTL" methods include chemical ligands, hormones, antibodies, antibody fragments, oligonucleotides, antigens, polypeptides, glycolipids, proteins, protein fragments, enzymes, peptide nucleic acids (PNAs), and polysaccharides. Examples of suitable tethers include, without limitation, single bonds, single divalent atoms, divalent chemical moieties of up to approximately 100 carbon atoms in length, multivalent chemical moieties, polyethylene, polyethylene oxides, polyamides, non-polymeric organic structures of at least about 7–20 carbon atoms, and related materials. Suitable quenchers include methyl viologen, quinones, metal complexes, fluorescent and nonfluorescent dyes, and energy accepting, electron accepting, and electron donating moieties. These examples of the ligand, tethering elements, and quenchers are not to be construed as limiting, as other suitable examples would be easily determined by one of skill in the art.

Polymer-Polymer Ensembles and Their Application to Biosensing

Figure 2:
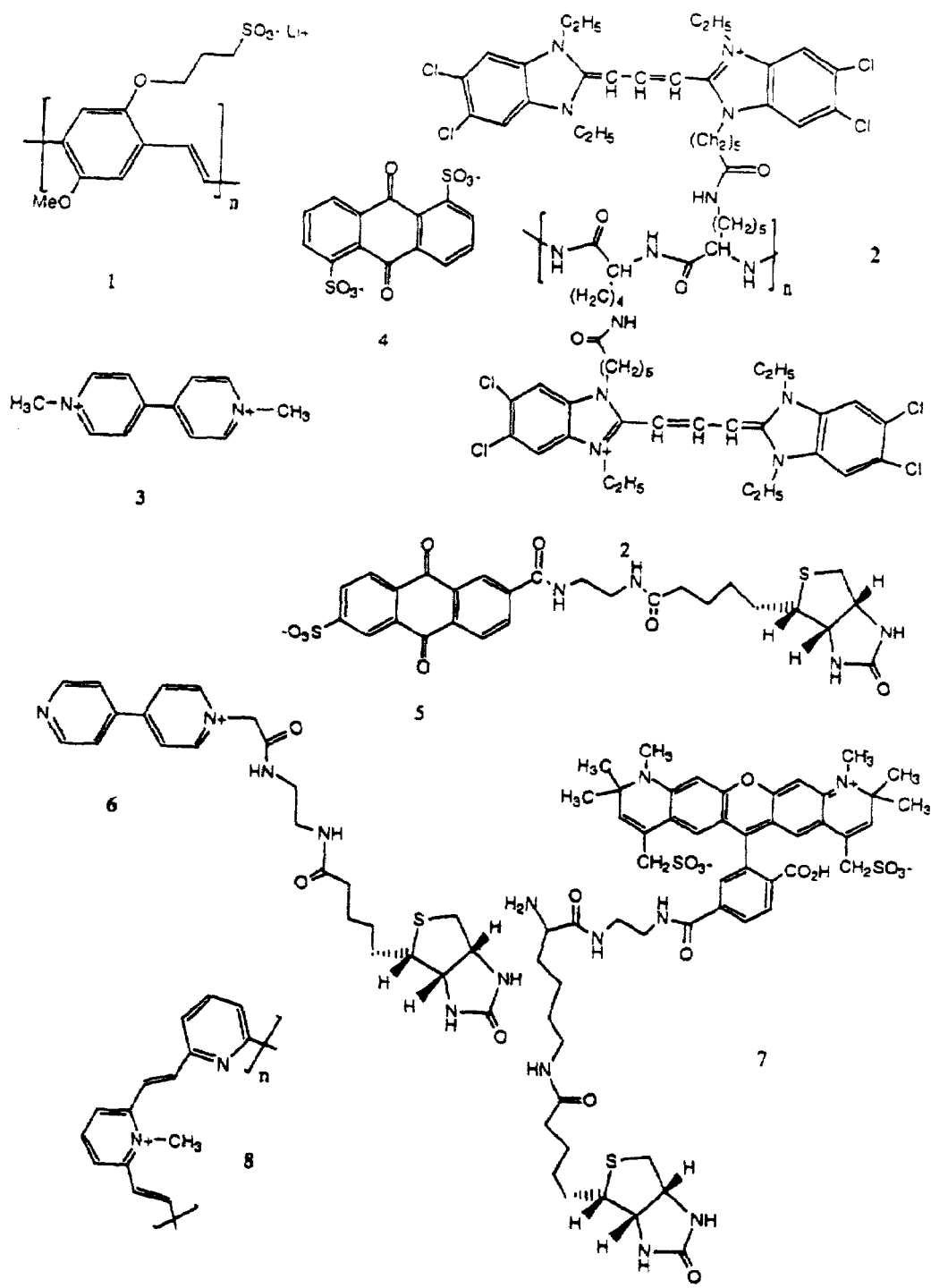
FIG. 2 illustrates various fluorescent compounds, quenchers, and QTL conjugates used in the present invention.

The fluorescent polyelectrolytes typified by compounds 1 and 2 in FIG. 2 show, in addition to their adsorption properties, a very strong tendency to associate with oppositely charged macromolecules, including other polyelectrolytes and each other. Cationic conjugated polymer 8, together with compounds 1 and 2, form a series of three fluorescent polyelectrolytes with absorption maximum wavelengths that span the range from the near ultraviolet to the visible-infrared, especially by varying the cyanine substituent in compound 2.

The association of two oppositely charged fluorescent polyelectrolytes can lead to several interesting and potentially useful effects considering the association of compounds 1 and 2. For example, the association of nearly equimolar, in repeat units, amounts of compounds 1 and 2 results in an ensemble that is overall close to neutral, yet consists of discrete regions of negative and positive charges. Since compound 2 shows an emission at lower energies than compound 1, it is observed that energy transfer should occur. Thus, excitation into regions where the absorption should be primarily by compound 1 results in predominant emission by compound 2. Since compound 2 has a very sharp emission, the harvesting of energy within the ensemble provide possibilities to tune both the absorption and emission properties far beyond that which is available within a single polymer. A most striking advantage obtained by using an ensemble such as the combination of compounds 1 and 2 is that both anionic and cationic small molecule quenchers can quench the overall near-neutral polymer mixture. As a result, it is observed that the ensemble is quenchable (independently) by both anionic compound 4 and cationic compound 3. More importantly, the quenching can be observed at very low concentrations of either quencher such that the degree of superquenching shows only a slight attenuation compared to quenching of the individual polymers by the oppositely charged small molecule.

These results show that the polymer-polymer approach offers distinct advantages for biosensing by the polymer-QTL method. The polymer ensemble can be quenched by both positive and negatively charged QTL bioconjugates. Therefore, either in quench/unquench formats or in a competitive assay, the polymer-polymer ensemble provides a means of obtaining higher selectivity and specificity. Furthermore, the degree of quenching by either cationic or anionic quenchers can be tuned directly by varying the stoichiometry of the polymer mixture. For example, when polymer 1 and polymer 2 are mixed in a ratio of 100:1, the superquenching by cationic QTLs is maintained and no quenching by anionic QTLs is observed. However, efficient energy transfer is still observed to polymer 2 even at this low ratio. By going to a 2:1 ratio of polymer 1: polymer 2, superquenching by both cationic and anionic QTLs is observed. Thus, charge tuning of the QTL assay is achieved by altering the stoichiometry of the anionic and cationic polymer. Both the net charge of the supramolecular cluster and the energy transfer characteristics of the combination may be tuned in this manner.

Multiplexed Detection Using Mixtures Containing Supported Polymer

The interaction of anionic and cationic fluorescent polymers can be eliminated by first anchoring either polymer to a bead or other supported format. For example, it has been demonstrated that anchoring polymer 2 to a clay suspension, prior to the addition of polymer 1 prevents the association of polymers 1 and 2. In this way, independent superquenching of each polymer is achieved in a single solution upon addition of either cationic or anionic quenchers.

Supported Formats for Monomers, Oligomers and Polyelectrolytes

Fluorescent polyelectrolytes, including conjugated and J-aggregate polymers, can be used for sensitive biodetection and bioassays in solution formats. The basis of this detection is the combination of the "superquenching" sensitivity of these molecules to quenchers of opposite or neutral charges with the synthesis of a quencher-recognition conjugate (QTL). One improvement of the polymer-QTL approach involves anchoring the fluorescent polymer onto a solid support via adsorption. Several advantages can result from this adsorption.

Figure 3:
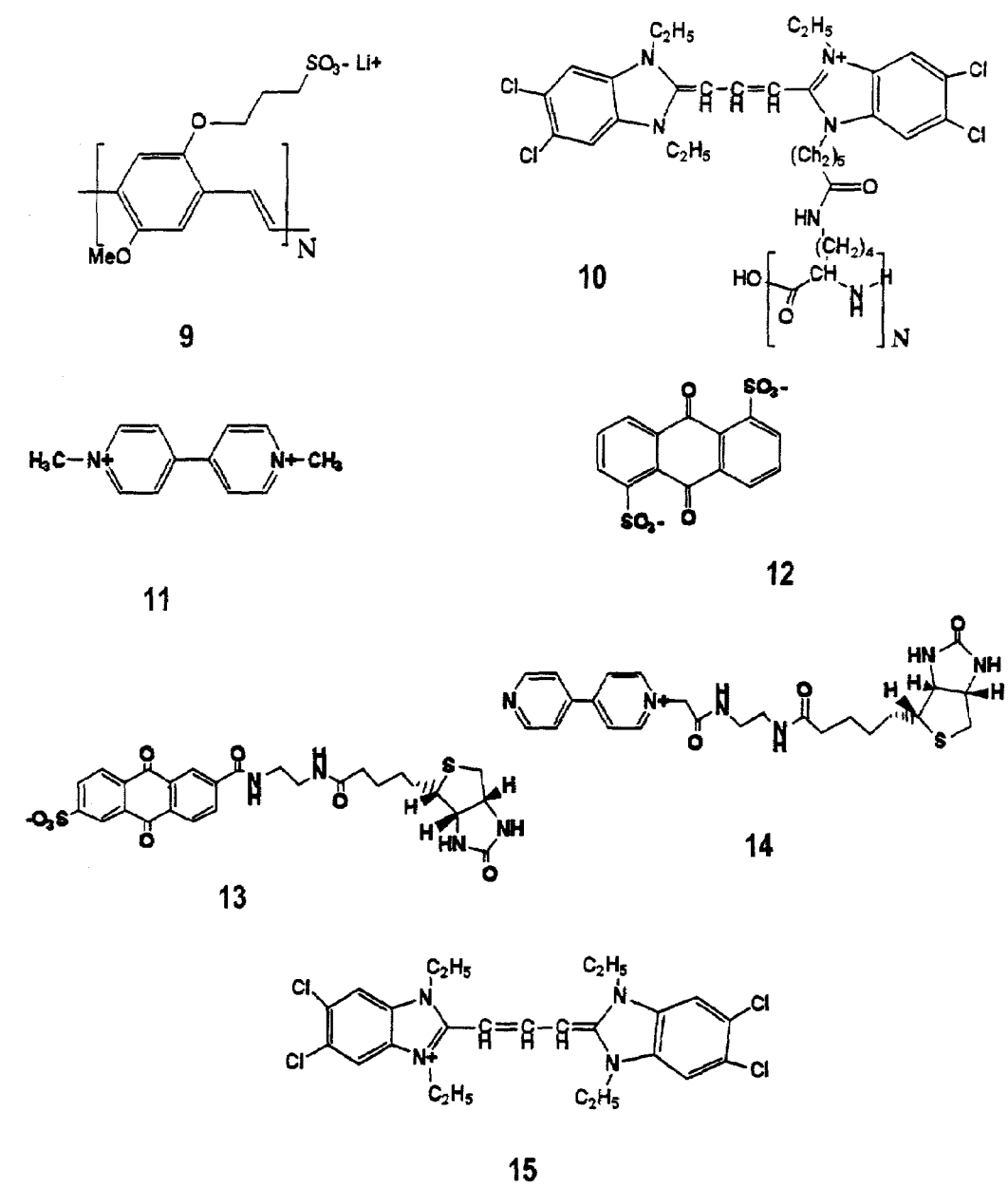
FIG. 3 illustrates various fluorescent compounds, quenchers, and QTL conjugates used in the present invention.

Fluorescent polyelectrolytes, including, but not limited to, compounds such as those shown in FIGS. 2 and 3 may be readily adsorbed from aqueous or mixed aqueous-organic solutions onto oppositely charged surfaces such as slides, plates, oppositely charged polymer beads (such as, but not limited to, quaternary amine-derivatized polystyrene or sulfonated polystyrene), and natural or synthetic inorganic supports such as clays or silica, charged membranes, or other porous materials. Once adsorbed onto these supports, the polymers retain their intense fluorescence as well as their sensitivity to specific quenchers. The fluorescent polymers incorporated into these formats may be used in advanced assays as described below.

The incorporation of a fluorescent polymer onto a charged polymer bead can result in the reversal of the charge specificity in quenching of the polymer fluorescence as well as in improved performance in assays involving the polymer in either fluorescence quench or fluorescence unquench modes. In one example, the anionic conjugated polymer 1 is effectively quenched by low concentrations of the positively charged electron acceptor 3 in aqueous solution. However, its fluorescence is largely unaffected in solution by the addition of the negatively charged electron acceptor 4. When polymer 1 is treated with a suspension of quaternary amine (cationic) derivatized polystyrene beads (Source 30 Q), the polymer is removed from solution and is irreversibly adsorbed onto the beads. In this supported format, the highly fluorescent beads can be suspended in an aqueous solution and treated with the same quenchers. A reversal of the quenching sensitivity is observed; in the supported format, the anionic electron acceptor 4 quenches polymer 1, while the fluorescence of polymer 1 is no longer quenched by cationic electron acceptor 3.

The charge reversal of fluorescence quenching can be adapted to biosensing by the polymer-QTL approach. Thus, QTL conjugate 5, which contains an anthraquinone quencher similar to anionic electron acceptor 4 and a biotin ligand, is also observed to quench the fluorescence of polymer 1. Upon addition of the protein avidin (a specific receptor for biotin), the quenching produced by conjugate 5 is reversed and virtually complete recovery of the fluorescence of polymer 1 is observed. This contrasts with aqueous solutions where a viologen-based conjugate 6 has been shown to elicit a similar quench-recovery response with polymer 1. For both polymers 1 and 2, when dissolved in aqueous or partially aqueous solutions, nonspecific effects are frequently observed upon the polymer fluorescence by addition of macromolecules, particularly proteins leading to either partial quenching or enhancement. These interactions may occur with analyte proteins or with proteins not anticipated to interact with the specific QTL conjugate employed in the sensing and may interfere with specific effects due to the interaction of an "analyte" protein with the polymer QTL complex. These nonspecific effects maybe eliminated or attenuated by employing polymers in supported formats.

A second example involves the use of the QTL conjugate 7, which quenches the fluorescence of polymer 1 by energy transfer. While anionic compound 7 does not quench the fluorescence of anionic polymer 1 in pure aqueous solutions, adsorption of polymer 1 on beads results in its quenching upon the addition of compound 7 and fluorescence recovery upon addition of avidin.

Adsorbing a fluorescent polymer on a charged support may not always lead to charge reversal in the quenching of the polymer. The charge reversal, or lack thereof, can be tuned by the degree of "loading" of the polymer onto sites on the support. In a different example, it is demonstrated that enhanced quenching can be obtained for a supported polymer as a consequence of adsorption. Thus, when cationic polymer 2 is adsorbed onto anionic Laponite clay particles, the polymer fluorescence is still subject to quenching when small amounts of anionic acceptor 4 are added to the aqueous suspension. Under these loading conditions, polymer 2 is not quenched by cationic acceptors such as compound 3. Quantitative analysis of the extent of quenching by compound 4 under these conditions indicates that the clay-supported polymer 2 is quenched more effectively (in this example by more than 30%) than when it is in a pure aqueous solution. This example illustrates two concepts that lead to improved biosensing with the polymer-QTL approach using supported polymers. The first concept is that the supported polymer can be used to "sense" oppositely charged quenchers when supported on the clay particles and yet exhibit improved stability with respect to degradation and precipitation (observed for aqueous solutions). When the same polymer is supported on the clay at lower loading levels, its fluorescence is quenched by cationic compound 3, thus demonstrating a charge reversal similar to that cited above with polymer 1. The second concept from these experiments with clay-supported polymer 2 and its quenching by compound 4 is that increased quenching sensitivity can be obtained due to polymer-polymer association effects on the clay particles. This increased quenching sensitivity may result from an increase in the J-aggregate domain (or conjugation length for conjugated polymers).

The combination of enhanced quenching sensitivity and the ability to tune the quenching sensitivity in supported formats as described above greatly extends the potential of the polymer-QTL approach both in regards to sensitivity and versatility. Additionally, the anchoring of fluorescent polyelectrolytes on beads, surfaces, or membranes can expand the utility of the polymer-QTL approach. Thus, the strong adsorption of the polymers onto beads or membranes can provide detection of analytes in a "flow-through" mode using either liquid or vapor streams. Additionally, the tethering of the polymer onto plates in a multi-well array format by adsorption demonstrates the use of these formats in high throughput screening and rapid sampling applications. Furthermore, the elimination of nonspecific effects upon anchoring to a bead surface greatly enhances the practical usage of QTL-based assays.

Virtual Polymers Based on Covalent Attachment of Supramolecular Building Blocks

Enhanced superquenching provides a new means of obtaining superquenching from much smaller oligomers and even monomers in an adsorbed format. Thus, it is possible to synthesize polymer 2 in a range of repeat unit sizes varying from n=3 to n=1000. It would be anticipated that, to a first approximation, in solution, the higher molecular weight polymers should exhibit higher quenching efficiencies due to an "amplification factor" that should be directly proportional to the number of repeat units (6). However, as the number of repeat units increases, the solubility of the polymer decreases and the complexity of the polymer allows new channels for nonradiative decay to attenuate the effectiveness of quenchers. Therefore, in the case of polymer 2, the potential for attaining maximum sensitivity by using very high molecular weight polymers cannot be recognized. The use of smaller oligomers (or even monomers) in an adsorbed format permits the construction of effective higher order polymers by the formation of extended aggregates that bridge across adjacent polymer (or monomer or oligomer) molecules. This provides for enhanced levels of superquenching and thus new sensors of greatly enhanced sensitivity.

Assembly of cyanine dye monomer 15 or oligomers 10 on silica or clay nanoparticles results in the formation of "J" aggregates that exhibit high superquenching sensitivity (i.e., surface activated superquenching) to ionic electron transfer or energy transfer quenchers. This can be attributed to a combination of high charge density (and resulting Coulombic interactions) and excitonic interactions within the self-assembled units. These assemblies also can be used as biosensors in the QTL fluorescence quench-unquench mode. These virtual polymers can be easily assembled from a variety of monomer or small building blocks, often bypassing difficult steps of polymer synthesis, purification, and characterization. Although studies to date have shown self-assembled virtual polymers to be relatively stable with little sensitivity in their fluorescence to added macromolecules, it is clear that the small adsorbed units may be subject to desorption or rearrangement under certain conditions, most notably high ionic strength. An approach that combines the simplicity of using small building blocks assembled on a surface with a more robust analysis platform involves the covalent tethering of monomers on the surface of a neutral or charged nanoparticle, bead, or other rigid support.

In one example, a relatively simple synthetic scheme similar to that developed for the cyanine poly-L-lysine 10 was employed in the construction of cyanine dye 15 covalently attached to the surface of 0.2 μm diameter silica microspheres. The cyanine dye thus linked to the microsphere surface was found to exist both as small clusters of the monomer and as highly ordered aggregates. Efficient exiton migration/energy transfer between the dye clusters and aggregates was observed when the material was suspended in water containing 2% dimethylsulfoxide. The suspension also showed a 27% reduction in emission intensity in the presence of 27 nM anionic quencher 13, indicating that superquenching of the covalently-linked dye assemblies occurs. The modes of interaction between cyanine dye monomers on the microsphere may be controlled by varying the density and structure of functional groups present on the surface. Thus, the efficiency of biosensing can be optimized. Similar schemes may be used to append other cyanine dyes and other building blocks such as conjugated polymer oligomers onto a bead, particle, or other solid surfaces.

Virtual Polymers Appended onto Quantum Dots by Self-Assembly or Covalent Tethers: Coupling of Quantum Dots with QTL Bioassays The assembly of cyanine dyes (including, but not limited to, the chromophore of structures 10 and 15) or other molecules capable of forming aggregates onto a particle or surface provides a platform for biosensing based on superquenching. The superquenching can be controlled by the charge of the assembled film or the surface or a combination thereof. Biosensing may be accomplished either by fluorescence "turn-on" or "turn-off" assays and in direct and competition modes. While the assembly may have relatively strong light-absorbing properties, in a number of cases, the absorption of J-aggregates is very sharp and limited to a very narrow portion of the visible spectrum. A significant enhancement of light-harvesting properties may be obtained by constructing the assembly on top of a layer or particle having strong absorption (and high oscillator strength) at higher energies. This can be accomplished in Langmuir-Blodgett Assemblies and complex multilayered films built up by layer-by-layer deposition.

The construction of an assembly of dyes or other molecules on a surface-capped semiconductor nanoparticle "quantum dot" offers a convenient and effective way of enhancing the biosensing capabilities of the virtual polymers described above. Although quantum dots have been investigated for several years, recent advances have made possible the preparation of quantum dots of high stability, variable size, versatile wavelength tunability for both absorption and emission properties, and controlled surface properties and functionality. Thus, it is possible to use an appropriately constructed and derivatized quantum dot as a support on which to construct a virtual polymer. The quantum dot "platform" is selected to have good energy donor properties towards a specific cyanine dye, cyanine dye aggregate, conjugated polymer oligomer, or other building block that can be used in a QTL bioassay. The combination affords an attractive, versatile, yet relatively simple way of enhancing the sensitivity and extending the wavelength range of the QTL biosensor. Both direct adsorption onto the quantum dot or covalent attachment or anchoring of dots and polymers on a microsphere surface may be used to construct the quantum dot-sensing ensemble. Examples of quantum dots include (but are not limited to) CdS, CdSe and ZnS.

QTL Bioassays Based on Assemblies and Inclusion Complexes of Dye Monomers, Oligomers, and Conjugated Polymer Oligomers in Natural and Functionalized Polysaccharides A wide range of investigations have shown that the starch-derived polymers amylose and carboxymethylamylose (CMA), which consist of linear, unmodified or derivatized 1,4 glucose polymers, can form complexes with hydrophobic or amphiphilic molecules that can exist as moderately linear conformations. The complexed "guest" amphiphiles exhibit restricted mobility and, in some cases, a degree of protection from other reagents present in the same solution with the amylose (or CMA) and its guest. The entrapment is attributed to formation of a helical sheath of the glycoside which surrounds a guest within the cavity. Helices with different radii can be formed to entrap guests of different sizes. Unmodified amylose is overall neutral while CMA (which is reasonably easily synthesized with variable loading of the carboxymethyl groups) is anionic. Analogous derivatization processes are possible to prepare amylose derivatives with other functionalities and/or charge. Several amphiphilic or hydrophilic molecules incorporating dyes or aromatic chromophores and exhibiting low solubility in water or aqueous-organic mixtures can be solubilized in amylose or CMA solutions with the guest chromophores entrapped within amylose (or CMA). Among examples of the latter are photo- and thermochromic dyes, highly luminescent stilbene amphiphiles, and other photoreactive compounds.

Figure 4:
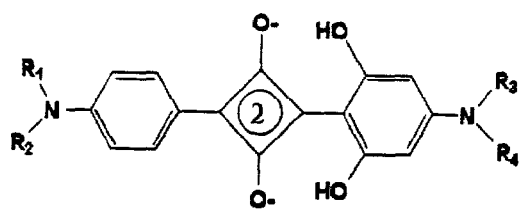
FIG. 4 illustrates structures of dyes used with polysaccharides in inclusion complexes.
Figure 4:
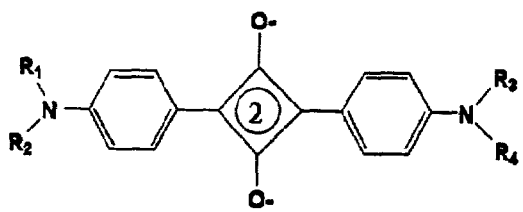
Figure 4:
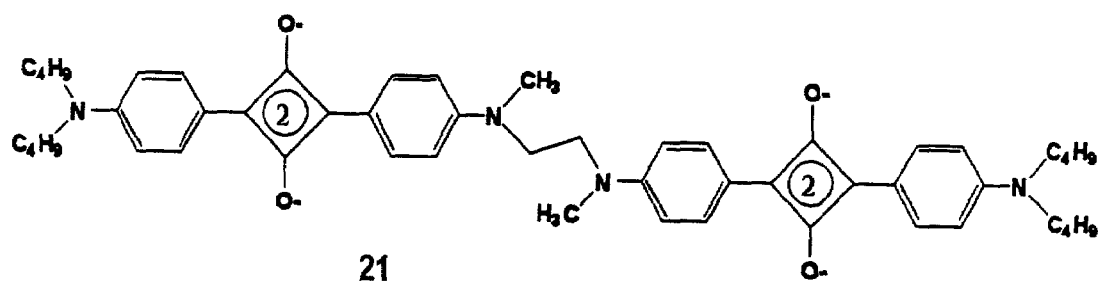
Figure 4:
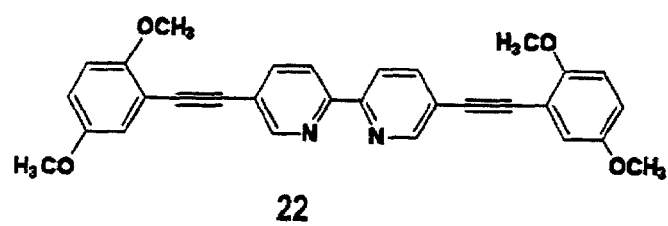

Amylose, CMA, and other polysaccharides can form complexes with strongly absorbing amphiphilic molecules including appropriately derivatized squaraine dyes, bis-squaraines, and some conjugated polymer oligomers such as poly (phenyl)ethynyl oligomers. Structures of some of these compounds selected are shown in FIG. 4. In each case, the compounds are either actually or potentially highly fluorescent in homogeneous solution. Additionally, they are either insoluble in water or very slightly soluble. Structurally they are able to form complexes with either amylose, CMA, or other modified amylose polymers. When incorporated with a charged amylose polymer, they become soluble in water, strongly fluorescent, and somewhat protected from association (such as face-to-face interactions which quench fluorescence) and adventitious quenching by nonspecific interactions with other solutes. The ability of the amylose and CMA hosts to collect multiple guests allows the gathering of several molecules of the host chromophores shown in FIG. 4. The high oscillator strength of the chromophores allows excitonic interactions to occur even when the chromophores are not in direct contact. These excitonic interactions provide a way of forming another "virtual polymer" similar to those described above. This virtual polymer may be subject to quenching by electron transfer or energy transfer quenchers that are brought into close proximity with the amylose or CMA helix containing the guest dyes or oligomers. This association may be obtained through Coulombic interactions between the quencher and complex or by other interactions that lead to strong association. Targeted superquenching by these quenchers can thus be obtained for included molecules such as those shown in FIG. 4, even when the individual molecules are not subject to superquenching. As described above, it is straightforward to extend superquenching to the use of QTL bioconjugates and to apply these bioconjugates in extensions of the QTL fluorescence quench-unquench and competitive assay formats.

The present invention is a further extension of the use of superquenching in biosensing. By co-locating a bioreceptor and a fluorescent polymer (or "assembled polymer") on a surface or colloidal particle, the interaction between the two components (quencher (Q) of the QTL and the polymer ensemble) is rendered a specific interaction by the ligand-receptor binding. Thus, the assay is not dependent upon nonspecific charge-based interactions between the quencher and the polymer ensemble. An additional advantage of the present invention is the versatility afforded by the ability to control the co-located assembly of a specific polymer ensemble-receptor either spatially (for example, on a rigid support) or on different particles. This greatly expands the ability of the QTL approach to be used for multiplexing several target agents.

All of the assay formats of this invention rely on a co-location of a fluorescent polymer (or fluorescent "self-assembled" polymer assembly) and an appropriate receptor for a target analyte on a support. The support can be a microsphere or nanoparticle, a membrane, cuvette wall or the surface of a microtiter plate or glass slide, or any surface that may be interrogated by continuous or intermittent sampling (illumination/detection). The direct advantage of this approach is that in each case, the superquenching occurs due to a specific ligand-receptor interaction. Several different examples are discussed in the following sections. Further, the assays may be carried out in operationally different formats depending upon the specific requirements.

Displacement Competition Assay

Figure 5:
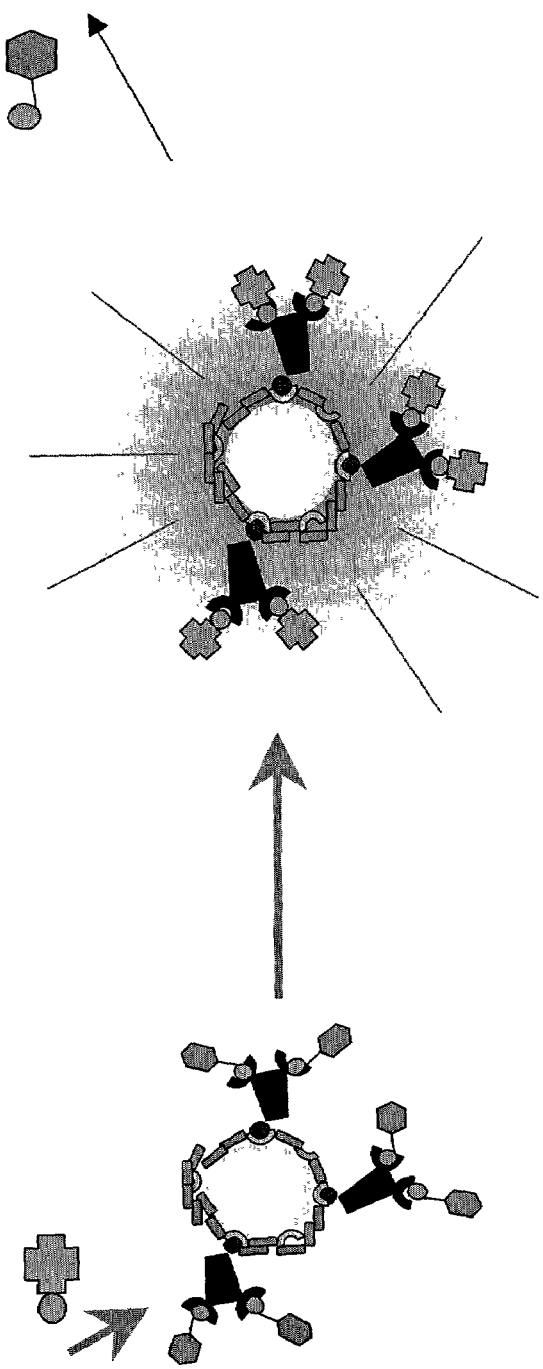
FIG. 5 is a general illustration of a displacement competition assay.

In the Displacement Competition Assay, the anchored fluorescent polymer-receptor is pretreated with the QTL conjugate, resulting in the binding of the QTL conjugate to the receptor and concurrent superquenching of the fluorescent polymer. As shown in FIG. 5, the actual analysis involves the addition of an analyte to the ensemble. The fluorescence of the polymer increases quantitatively (turn on) with the level of the target agent in the analyte sample. Suitable examples include proteins, viruses, bacteria, spores, cells, microorganisms, antibodies, antibody fragments, nucleic acids, and toxins. In this example, the assay may be homogeneous and the actual time for the assay may be controlled by the "off rate" of the QTL from the receptor.

Direct Competition Assay

Figure 6:
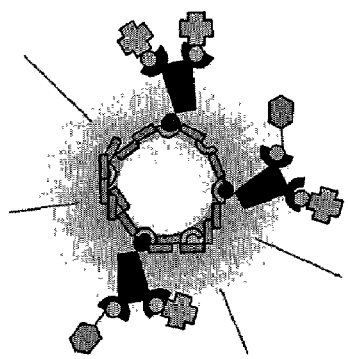
FIG. 6 is a general illustration of a direct competition assay.
Figure 6:
Figure 6:
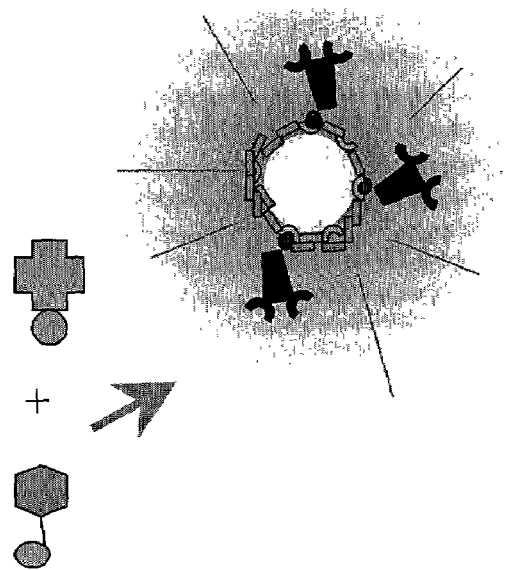

As shown in FIG. 6, in the Direct Competition Assay, the anchored fluorescent polymer-receptor is treated with a mixture containing an analyte (an unknown amount of the target agent) and a known amount of QTL conjugate. The polymer fluorescence is quenched to an extent determined by the QTL:target agent concentration ratio. The stronger the fluorescence, the higher the concentration of the target agent. An advantage of this approach used is that the assay may be both homogeneous and near instantaneous. Since both the target agent and the QTL conjugate compete directly for "open" receptor sites, the response can be very rapid.

In another formulation, the anchored fluorescent polymer-receptor is incubated with an analyte sample before the fluorescence intensity of the sample is measured. The sample is then treated (following rinse steps as necessary) with an excess of a QTL conjugate. The initial reading of fluorescence following treatment with the QTL conjugate shows quenching due to binding of the QTL conjugate to unoccupied receptor sites. The stronger the initial fluorescence quenching, the smaller the level of target agent. Monitoring the polymer fluorescence as a function of time provides additional confirmation of the binding of the target agent and its replacement by the QTL conjugate at the receptor.

A "Turn on" Competitive Assay Based on Polymer-Biomolecule Combinations

Polymers that contain reactive end groups (e.g., polymer 10) may be covalently linked to a variety of materials, including small molecules, other polymers, and biomacromolecules. The resulting "hybrid molecule" may have similar solubility and will generally have the same ability as the individual polyelectrolyte component to adsorb to a surface. These surfaces include slides or plates, oppositely charged polymer beads (such as, but not limited to, quaternary amine-derivatized polystyrene or sulfonated polystyrene), natural or synthetic inorganic supports such as clays or silica, charged membranes, semiconductor nanocrystals, and other porous materials. Thus, either independently or as a component of a mixture, the use of a hybrid molecule can afford the preparation of a supported assembly containing a highly fluorescent species subject to superquenching. The hybrid molecule may also be employed in a solution-phase assay.

Figure 7:
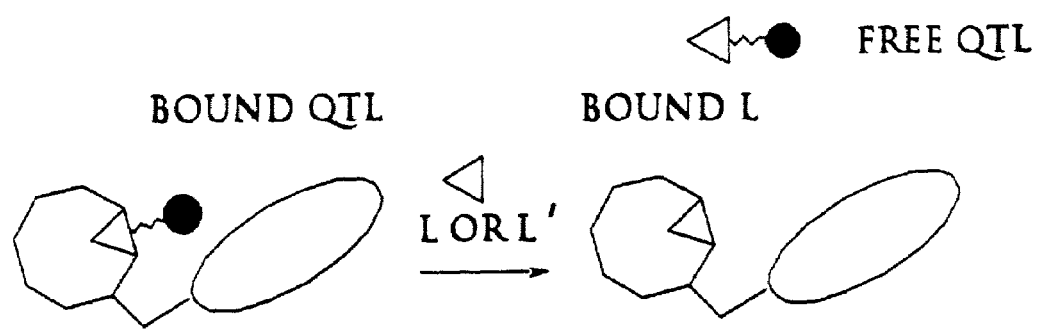
FIG. 7 is an illustration of the competitive fluorescence "turn-on" assay with the polymer-biomolecule combination.
Figure 7:
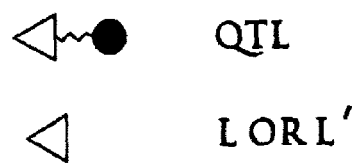

In one example, the carboxyl or amine terminus of an amino acid polymer such as polymer 10 may be linked to a primary amine of a protein or antibody or antibody fragment to give a fluorescent compound 23. (See FIG. 7). This compound can either be used in solution or can be deposited on a surface such as is described above. In either format, the biomolecule portion of compound 23 should retain its specific recognition function. Thus, treatment of compound 23 with a QTL bioconjugate results in formation of a complex that allows the quenching component to extinguish the fluorescence from compound 23. The exposure to molecules such as L or L' that can compete with the QTL binding site can result in displacement of the bound QTL bioconjugate and a turning on of the fluorescence from compound. The most effective utilization of compound 23 will generally be on a surface or bead or other supported format where the aggregation of the fluorescent species can result in enhanced superquenching sensitivity. The hybrid molecule thus serves as a molecular or supramolecular (in supported formats) sensor whose function is shown schematically in FIG. 7.

In another example, a sensor/assay may be achieved in a supported format by collecting individual (i.e., not covalently linked) polymer and biomolecule components on the same bead, particle, or nanostructure. For example, carboxyl functionalized beads or particles may be used both to covalently bind a protein, antibody, or antibody fragment via an amine group on the protein (as described above) and to bind a monomer (such as 15), oligomer or polymeric fluorescent dye such as 10 by adsorption or covalent attachment. Provided there is no significant quenching interaction between the dye ensemble and the biomolecule, the "dual coated" beads will be strongly fluorescent. Here again, a competitive fluorescence "turn-on" assay may be constructed by the use of a QTL bioconjugate that associates with the biomolecule. Further, the addition of the QTL bioconjugate will result in a quenching of the dye ensemble fluorescence. Addition of a reagent L or L' that can compete with the QTL bioconjugate for the binding site will result in the expulsion of the QTL molecule from the bead or particle and an increase (or unquenching) of the dye ensemble fluorescence. Because the spatial range for quenching is increased, a preferred embodiment will be the case where Q is an energy transfer quencher. This will allow the quenching of all polymers within the Foerster transfer radius of the receptor-bound QTL molecule. For polymers bound on surfaces, this radius can be approximately 100 Angstroms or more.

The dual coated beads or particles can also be used in a fluorescence "turn-off" competitive or noncompetitive assay. Treatment of the beads (initially uncomplexed) with an antigen (L or L') will result in the binding of the antigen to the biomolecule, but with negligible fluorescence changes. Addition of an aliquot of a QTL molecule that can bind, but not compete with L or L' will result in a quenching of the polymer fluorescence in a "turn-off" response, that is proportional to the number of receptor sites not occupied by the antigen. A QTL molecule that can compete with antigen L or L' will give a time-dependent response which can be used to measure both the level of antigen present and the strength of its binding to the biomolecule.

Figure 8:
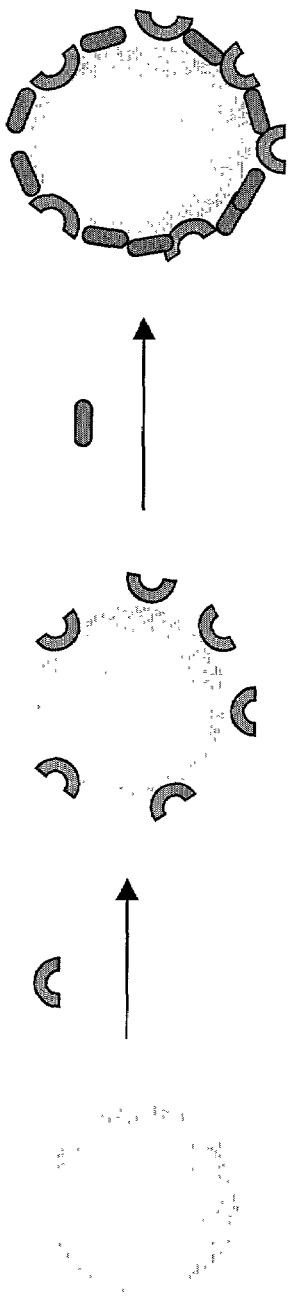
FIG. 8 illustrates the co-location of a polymer and a receptor by a covalent/adsorption sequence.
Figure 9:
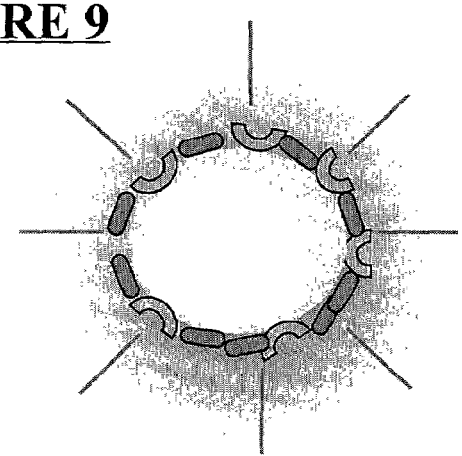
FIG. 9 illustrates the covalent tethering of both the polymer and the receptor binding site.
Figure 9:
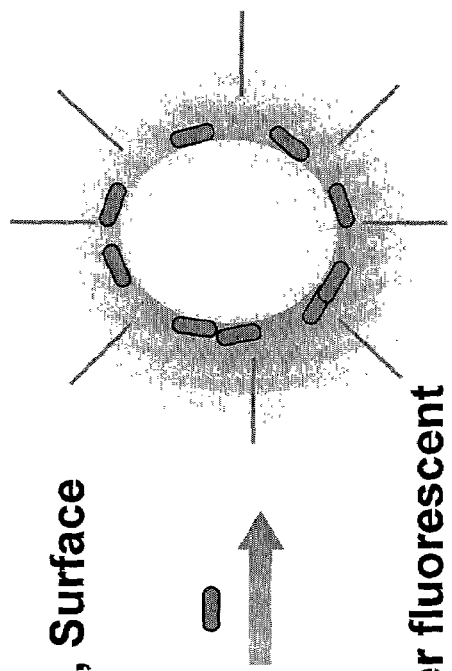
Figure 10:
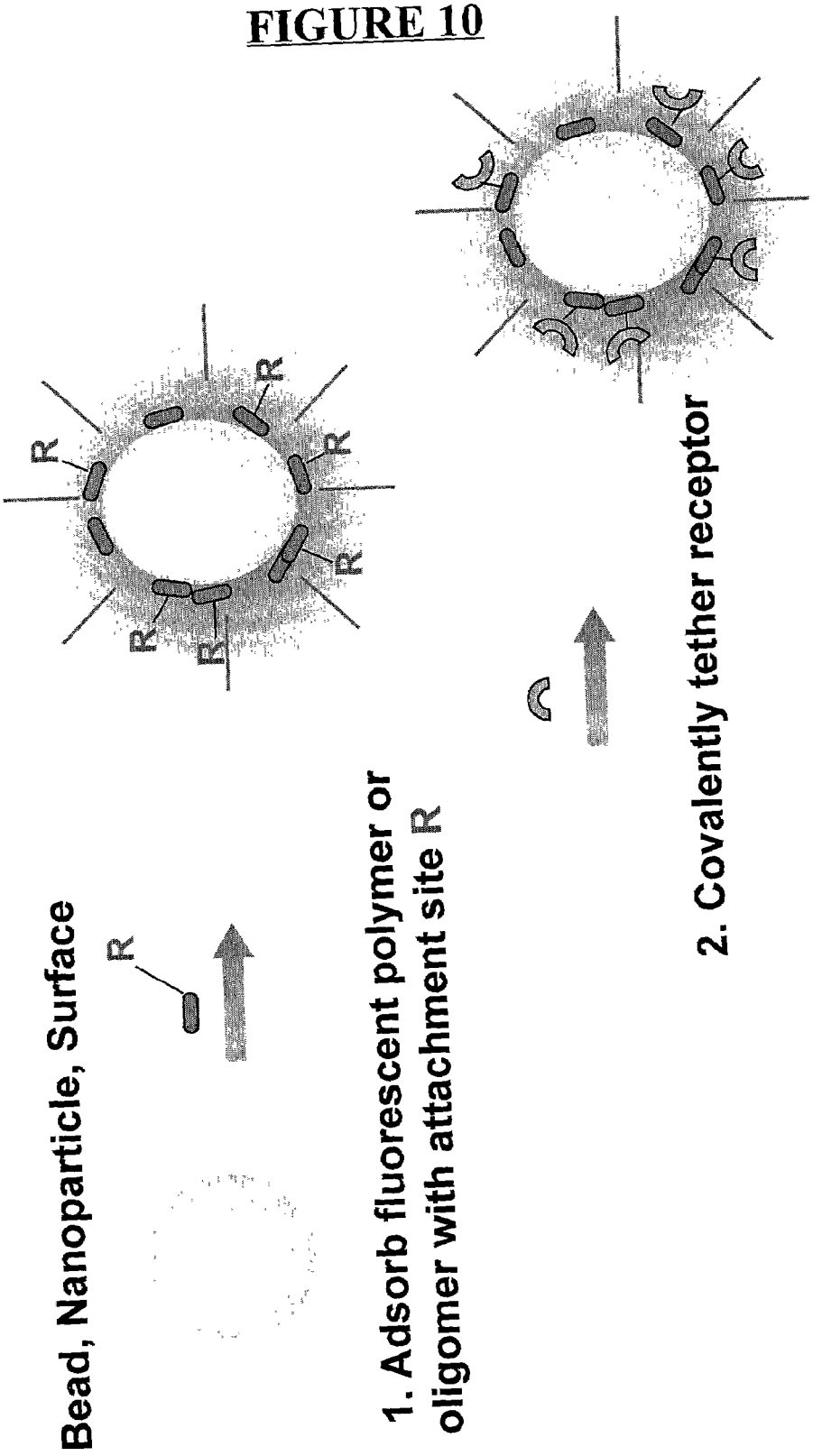
FIG. 10 illustrates a receptor covalently linked to a polymer.

The central component of the above-mentioned assays is the supported (and co-located) fluorescent polymer-receptor ensemble. They may be constructed (but is not limited to) as outlined in the following examples. In the first example, a receptor, or "receptor binding site" is covalently attached to a support. Subsequently a fluorescent polymer may be adsorbed onto the same support as illustrated in FIG. 8. Examples of receptors that may be covalently attached include proteins such as avidin, neutravidin or streptavidin or antibodies, peptides and nucleic acids. The degree of loading of both fluorescent polymer and receptor can be controlled to obtain sensors having varied sensitivity and dynamic range. In a second example, as shown in FIG. 9, both the polymer and receptor may be covalently tethered to the support. In another formulation, illustrated in FIG. 10, a polymer or oligomer doped with a reactive group is tethered to a receptor by a covalent linkage and adsorbed to a support. The polymer may be first adsorbed and then covalently linked to the receptor or vice versa. To take advantage of enhanced superquenching provided by "self-assembled" polymers, the fluorescent "polymer" ensemble can be constructed from monomers that may be collected by either self-assembly (adsorption) or covalent linkage. Depending upon the requirements of the assay and the component "polymer" and receptor, the receptor may be covalently linked to the support before or following generation of the self-assembled polymer.

Figure 11:
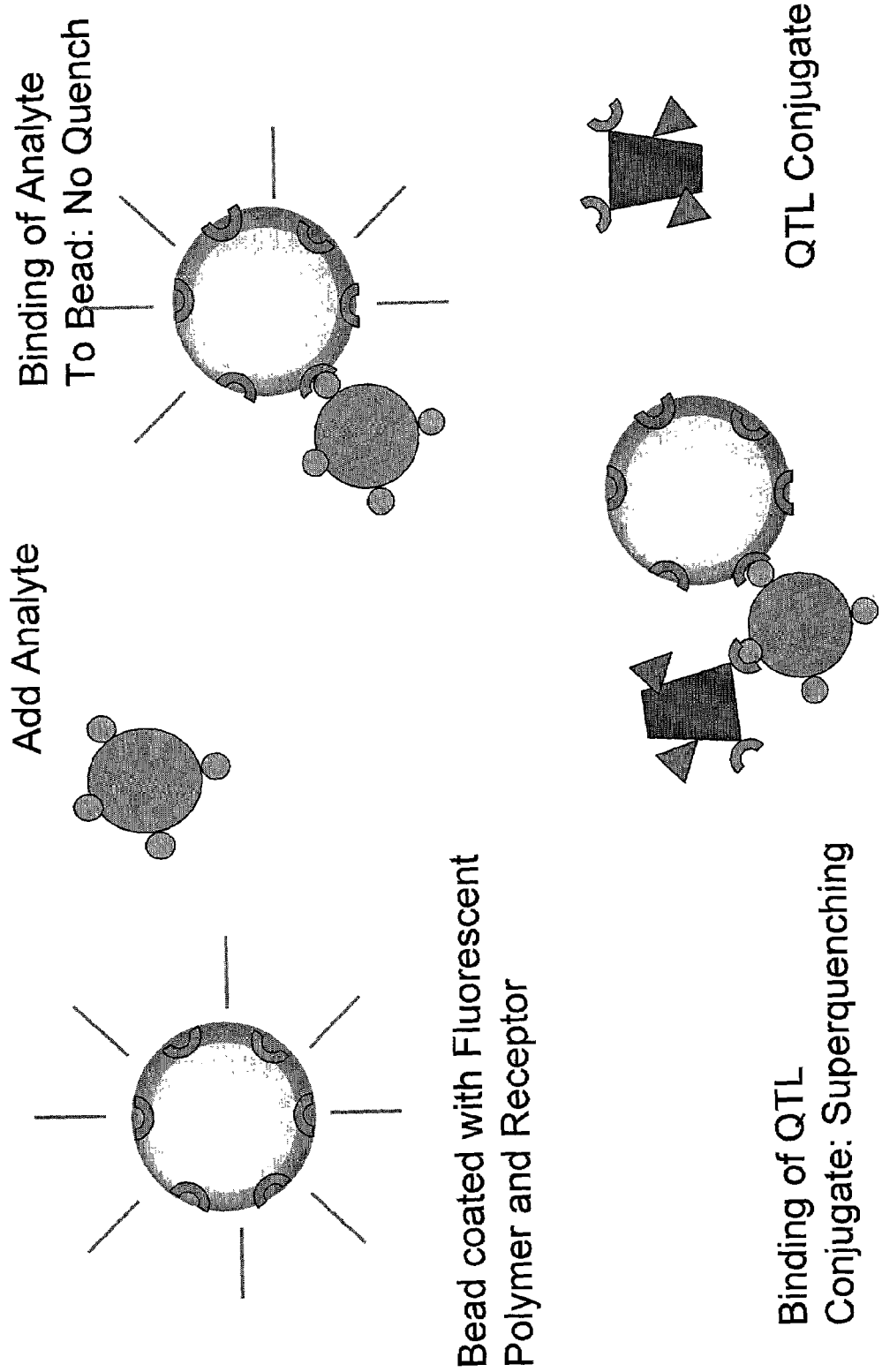
FIG. 11 is an illustration of a sandwich QTL assay.

In addition to the assays based on direct binding of a QTL conjugate to the fluorescent polymer-receptor ensemble, assays may also be constructed based on secondary recognition events. For example, the current platforms can be extended to a sandwich format in which a target agent having multiple binding sites for the same or other receptor is sensed. This format is illustrated in FIG. 11. Binding of the target agent to a receptor site causes little or no change in the fluorescent polymer fluorescence. However, addition of a QTL conjugate which also binds to the receptor results in bringing the quencher close enough to quench the fluorescence in a direct assay. Such a sandwich assay can be adapted to sense a variety of agents including bacterial spores.

Having generally described the invention, a further understanding can be obtained by reference to certain specific examples provided herein for purposes of illustration only and are not intended to be limiting unless otherwise specified.

EXAMPLES

Example 1

Figure 12:
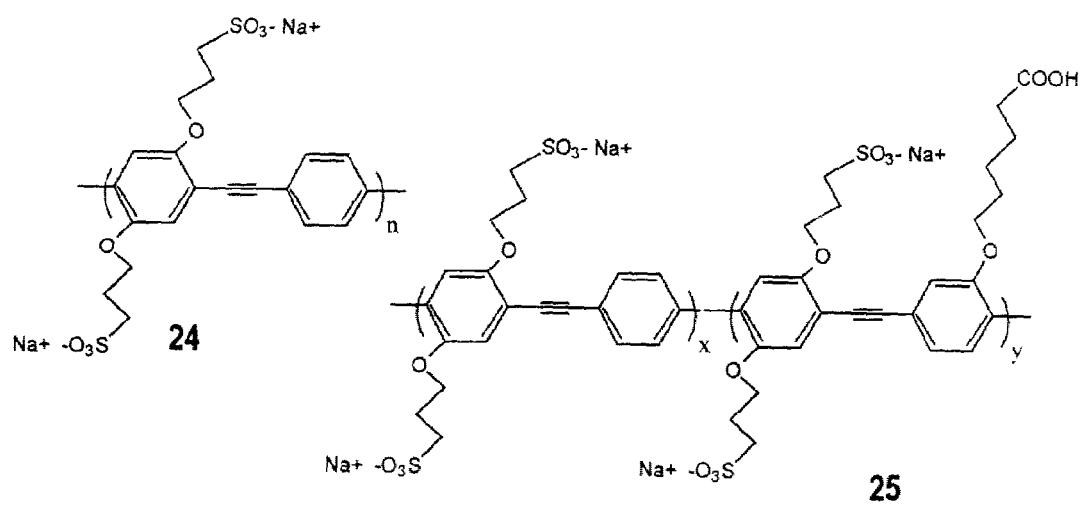
FIG. 12 illustrates various compounds used in the examples of the present invention.
Figure 12:
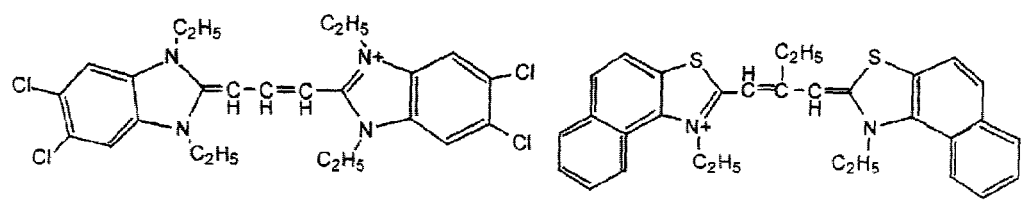
Figure 13:
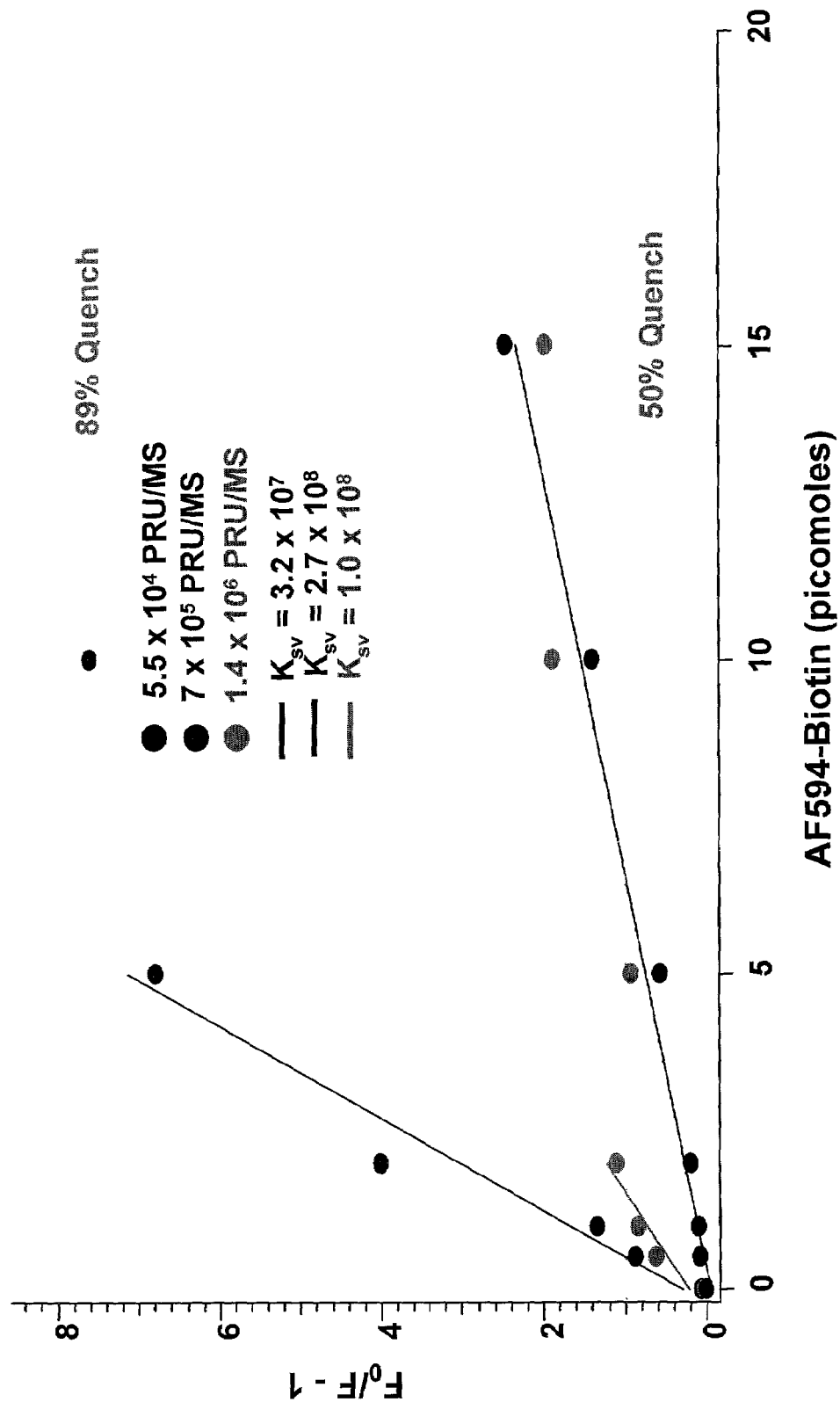
FIG. 13 is a graphical illustration of the quenching of fluorescence as a function of the loading level.

Commercial polystyrene beads containing streptavidin covalently tethered to the surface(0.53 micron microspheres purchased from Bangs Laboratories, Inc., Fishers, Ind.) were coated with the anionic conjugated polymer 24, a derivative of poly(phenyleneethynylene) (PPE) (structures 24–27 are shown in FIG. 12). The level of loading of 24 on the surface can be controlled depending on the loading of the polymer. The number of biotin binding sites (maximum biotin-FITC binding capacity=1.42 ug/mg of microspheres) is also variable and controllable. For an initial assessment of the ability of the coated microspheres to function in biosensing, a QTL conjugate formed of an energy transfer quencher (Alexafluor 594, purchased from Molecular Probes) was conjugated to the streptavidin ligand biotin. In separate studies it was demonstrated that nonspecific quenching of the polymer fluorescence by non-biotinylated Alexafluor 594 does not occur. Depending on the level of coating, the $K_{SV}$ was found to vary between $3\times10^7$ and $3\times10^8$ M$^{-1}$ over two logs of QTL concentration. The level of the QTL detected by direct binding to the receptor in a conventional 96-well plate was less than 100 femtomoles. For this assay, it was determined that an intermediate level of polymer loading onto the beads gave optimal initial quench sensitivity and a wide dynamic range. (See FIG. 13).

Figure 14:
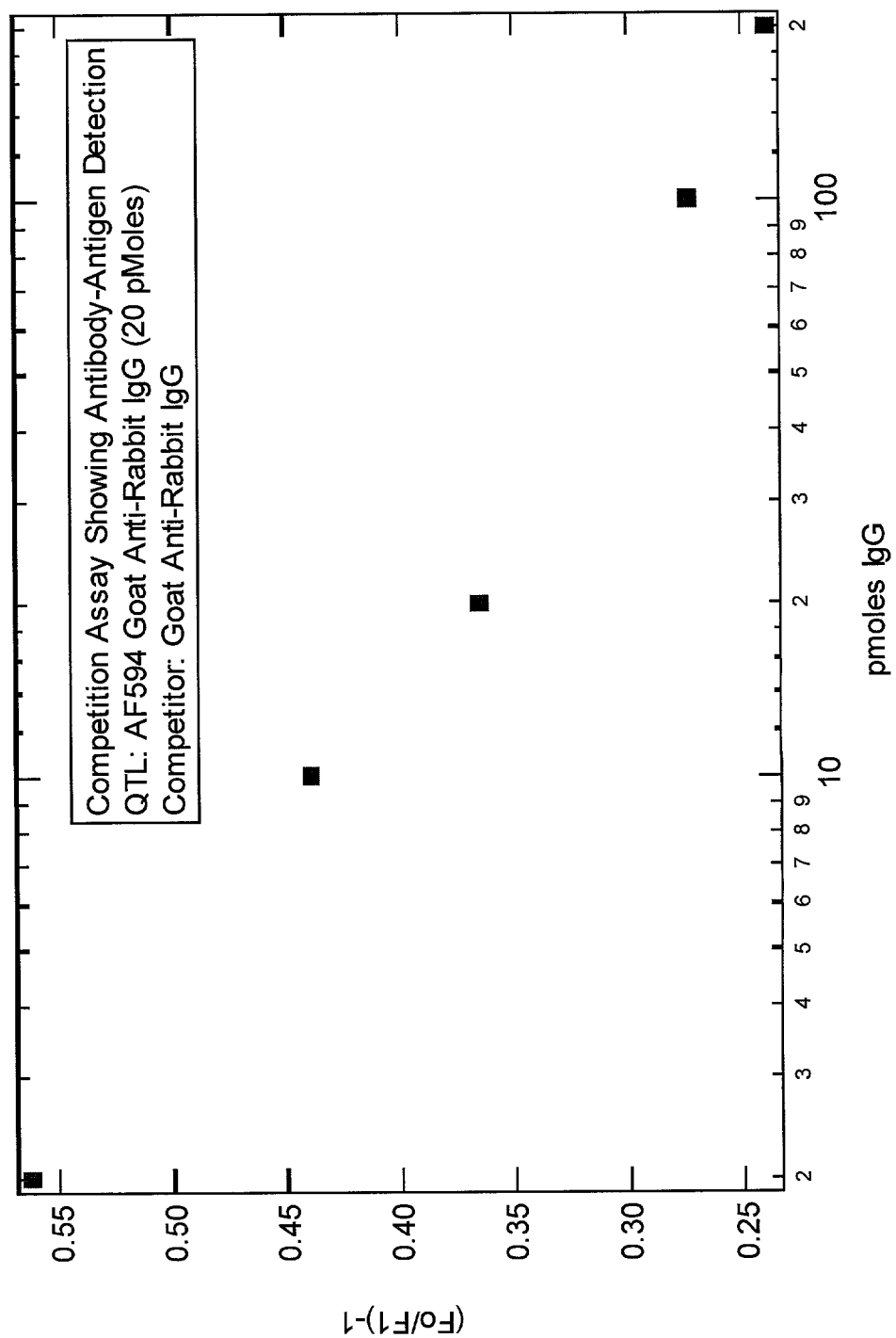
FIG. 14 is a graphical illustration of a competition assay for goat anti-rabbit IgG antibody.

To generalize the assay using these beads, biotinylated antibodies can be used to tether specific receptors. The binding of the biotinylated antibodies produces little change in the fluorescence of the polymer. However, the addition of a conjugate recognized by the antibody and containing an energy transfer quencher does result in quenching of the polymer fluorescence. Thus, as shown in FIG. 14, it has been demonstrated that a biotinylated capture antibody can bind to an antibody-based QTL conjugate (target antibody derivatized with an energy transfer quencher) and be detected at levels less than one picomole).

From this example, it is evident that the same beads can be used to construct a wide array of assays based on antibody-antigen interactions. In the general case, two additional components are required: a biotinylated antibody or other receptor and a QTL conjugate that is recognized by the antibody. All three of the assay paths described above can be used with these beads. The use of labeled beads (e.g., a polystyrene bead labeled in the interior of the bead with a fluorescent dye tag having distinct fluorescent wavelengths) or different polymers with different antibodies or receptors allows for the simultaneous assay of multiple target analytes.

Example 2

Figure 15:
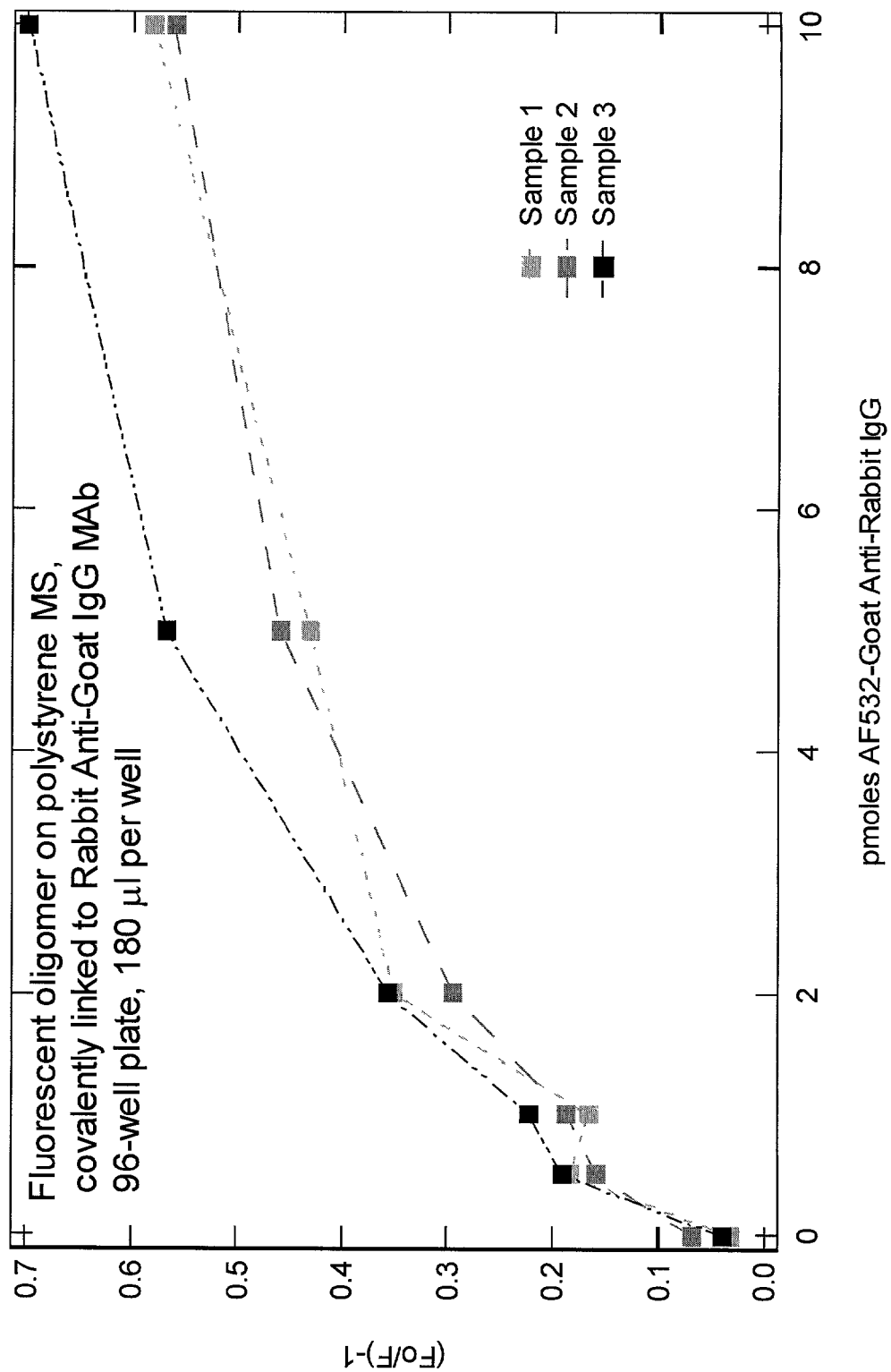
FIG. 15 is a graphical illustration of an IgG assay with polymer 25 linked covalently to a receptor.

A somewhat lower molecular weight PPE oligomer, monofunctionalized with carboxylate 25, was adsorptively coated on quaternary ammonium-derivatized polystyrene microspheres. Following deposition, rabbit anti-goat IgG antibodies were covalently linked to the polymer through the available carboxyl functionality. The fluorescence of the polymer remained strong following the antibody coupling and showed little sensitivity toward photobleaching. However, the fluorescence of the ensemble of oligomers was quenched specifically by the addition of goat anti-rabbit IgG conjugated to the fluorescent energy transfer quencher, Alexafluor 532. Fluorescence quenching could be detected at <500 fmole levels in a 96-well plate format. (See FIG. 15). Additionally, goat anti-rabbit IgG antibodies coupled with the nonfluorescent energy transfer quencher QSY35 also exhibited quenching on association with the bead-anchored polymer-antibody receptor. In this case, a $K_{SV}=8\times10^7$ M$^{-1}$ was measured in the sub to few picomoles concentration range.

Example 3

Cyanine dyes exhibit induced J-aggregation on anionic nanoparticles and microspheres. For simple cyanine monomers such as 26, adsorption onto clay or silica particles is reversible and thus individually coated particles coated with different cyanine dyes or cyanine mixtures exhibit exchange among the cyanines. It has been determined that the use of amphiphilic cyanine dyes such as the derivative of 26 where the N-ethyl groups have been replaced by N-octadecyl groups results in molecules that can be irreversibly adsorbed onto silica microspheres. Thus, individual amphiphilic cyanine dyes or mixtures of amphiphilic cyanines may be coated separately onto silica microspheres and then mixed with silica microspheres coated with other formulations of cyanine amphiphiles. The mixtures show no evidence of exchange of cyanines between different particles and thus permit the use of these mixtures for the simultaneous sensing of multiple agents. The use of energy accepting amphiphilic guests such as the corresponding amphiphilic cyanine to 4 results in the same emission wavelength shifting and affords the construction of several ensembles capable of emitting fluorescence at different wavelengths from the same host amphiphilic cyanine.

The fluorescence of the aggregated cyanine dye may be quenched by either cationic or anionic energy accepting cyanine dyes or by electron transfer quenchers. This quenching can be tuned by varying the level of coating of the cationic cyanine dye on the anionic nanoparticle or microsphere. At low loading of the particle with a cationic cyanine, the particle has regions of exposed negative charge and positively charged quenchers are attracted (and exhibit high superquenching constants) while potential anionic quenchers show low quenching via these nonspecific interactions. At high loading of the particles, the situation is reversed and anionic quenchers show attractive but nonspecific interactions and consequent high quenching constants while cationic quenchers are ineffective. For clay nanoparticles, optimum results occur with near 100% coverage of the clay surface by a cyanine or cyanine mixture. At this level of coverage, selective quenching by anionic quenchers occurs. For cyanine dye aggregates on the clay nanoparticles, the most effective quenching occurs when like-charged cyanines are co-adsorbed.

For example, the addition of energy accepting cationic cyanine 27 to excess cyanine 26 results in 50% quenching when the ratio of compound 26 to compound 27 ratio is 400:1. The quenching of 26 by 27 results in the sensitized emission of 27 and offers a potential advantage in separating the excitation and emission of the nanoparticle-supported ensemble. These particle-bound "self-assembled polymers" offer a convenient platform for sensing similar to those discussed above in Example 1 and 2. Coating of cyanine monomer or a mixture (such as 26 and 27) onto anionic microspheres or nanoparticles that already have a covalently anchored receptor such as streptavidin or an antibody can result in the formation of regions of J-aggregate or mixed aggregate on all accessible anionic surfaces of the support. This renders the ensemble overall slightly cationic and therefore of very low susceptibility to nonspecific association with cationic quenchers. However, cationic QTL conjugates can associate with the particles by specific ligand-receptor interactions in the same ways as described in the Examples 1 and 2 above. Thus, the superquenching of the self-assembled polymers can be harnessed in improved biosensing through specific association in the co-located receptor-self-assembled polymer ensembles.

Example 4

Figure 16:
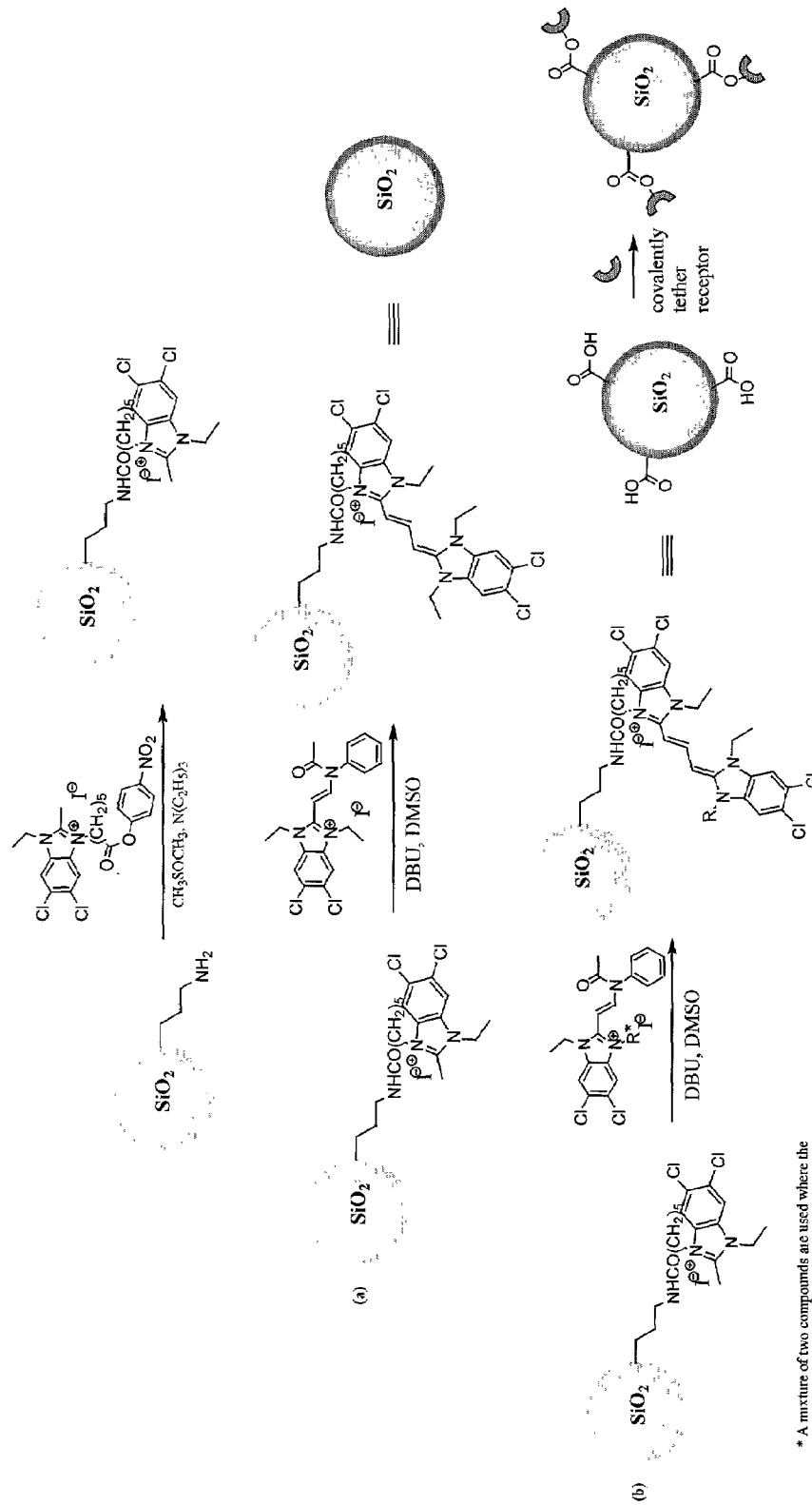
FIG. 16 illustrates the synthesis of cyanine dye 26 covalently appended to a silica microsphere surface.
Figure 17:
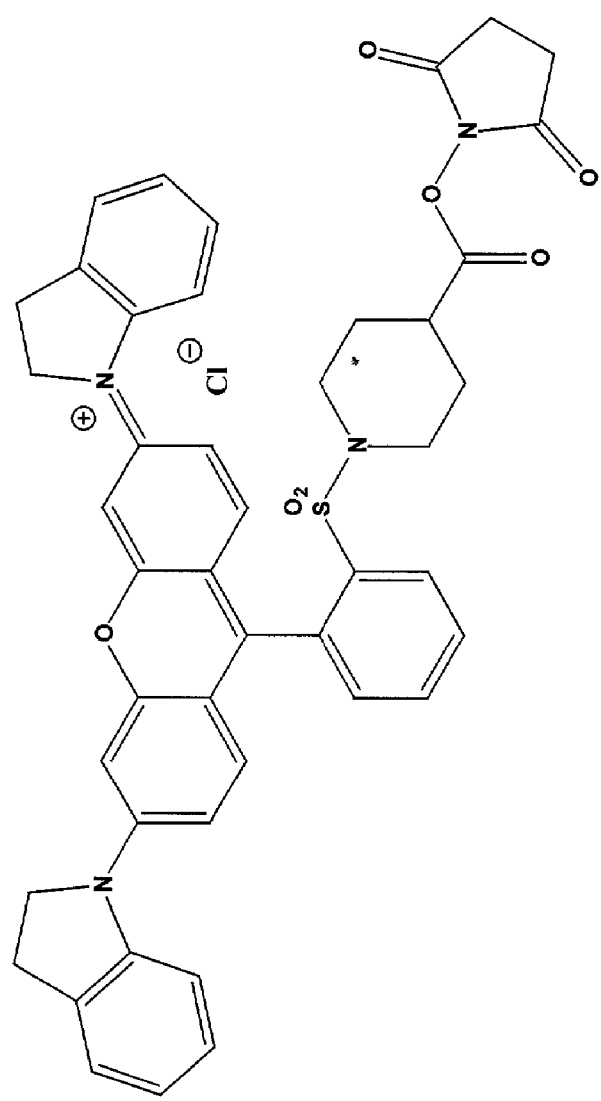
FIG. 17 is an illustration of the structure of QSY-21 Succinimidyl Ester.

The same kind of self-assembled polymers may also be constructed by covalent linkage of cyanine (or other monomers) onto a densely functionalized surface. As shown in FIG. 16a, the same cyanine chromophore present in 26 can be constructed by covalent attachment in two stages. It has been determined that amine functionalized silica microspheres can form a platform onto which a high level of coverage can be obtained. For microspheres coated only with the monomer, it is found that, depending on the surface derivatization and reaction conditions, different populations of at least three species are obtained. The first species has absorption and fluorescence close to those of the monomer. A second, longer-wavelength absorbing species shows very similar absorption and emission to the J-aggregate of 26 described above. The third species exhibiting a somewhat broadened emission at longer wavelengths is usually not prominent in absorption but frequently includes the predominant emission, regardless of the wavelength at which the mixture is excited. It has been found that quenching by non-specific interactions can be observed for anionic electron transfer dyes (AQS-Biotin (5) (FIG. 2), $K_{SV}=3\times10^7$ $M^{-1}$) and for a cationic energy transfer dye (QSY-21 (6)) (FIG. 17), $K_{SV}=5.3\times10^8$ $M^{-1}$) at subpicomole levels of quencher. In order to construct a sensor analogous to those described in the Examples above, the covalently-linked cyanine was constructed with varying amounts of an additional functionalized site containing a carboxyl group as shown in FIG. 16b. Once the dye has been tethered to the surface, the carboxyl sites may be used to append a receptor as outlined in Example 2 set forth above. The appending of a receptor on the surface of the covalently tethered "self-assembled polymer" has the advantage of shielding the dye from non-specific association with potential quenchers and restricting quenching interactions to QTL conjugates associating specifically with the receptor.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for the recitation of the claims set forth below.

REFERENCES

1. L. Chen, D. W. McBranch, H.-L. Wang, R. Helgeson, F. Wudl and D. G. Whitten, "Highly-Sensitive Biological and Chemical Sensors Based on Reversible Fluorescence Quenching in a Conjugated Polymer", Proc. Nat'l Acad. Sci. USA, 96:12287 (1999).

2. L. Chen, D. McBranch, R. Wang and D. G. Whitten, "Surfactant-Induced Modification of Quenching of Conjugated Polymer Fluorescence by electron Acceptors: Applications for chemical Sensing", Chem. Phys. Lett., 330: 27–33 (2000).

3. L. Chen, S. Xu, D. McBranch and D. G. Whitten, "Tuning the Properties of Conjugated Polyelectrolytes Through Surfactant Complexation", J. Am. Chem. Soc., 122:9302–9303 (2000).

4. D. Whitten, L. Chen, R. Jones, T. Bergstedt, P. Heeger, D. McBranch, "From Superquenching to Biodetection; Building Sensors Based on Fluorescent Polyelectrolytes" in "Molecular and Supramolecular Photochemistry, Volume 7: Optical Sensors and Switches", Marcel Dekker, new York, eds. V. Ramamurthy and K. S. Schanze, Chapter 4, pp 189–208 (2001).

5. R. M. Jones, T. S. Bergstedt, C. T. Buscher, D. McBranch, D. Whitten, "Superquenching and its applications in J-aggregated cyanine polymers", Langmuir, 17:2568–2571 (2001).

6. L. Lu, R. Helgeson, R. M. Jones, D. McBranch, D. Whitten, "Superquenching in cyanine pendant poly-L-lysine dyes: dependence on molecular weight, solvent and aggregation", J. Am. Chem. Soc., in press.

7. R. M. Jones, T. S. Bergstedt, D. W. McBranch, D. G. Whitten, "Tuning of Superquenching in layered and mixed fluorescent polyelectrolytes", J. Am. Chem. Soc., 123:6726–6727 (2001).

8. R. M. Jones, L. Lu, R. Helgeson, T. S. Bergstedt, D. W. McBranch, D. Whitten, "Building highly sensitive dye assemblies for biosensing from molecular building blocks", Proceedings Nat'l. Acad. Sci. USA, 98:14769–14772 (2001).

What is claimed is:

1. An assay for detecting the presence and or/amount of a target biological agent in a sample comprising:
   determining, in the absence of the sample, a fluorescence emitted by a composition comprising:
   (A) a fluorescer and
   (B) a receptor specific for both a target biological agent and a chemical moiety, wherein the fluorescer and the receptor are each affixed to a solid support;
   combining the composition with the sample and the chemical moiety; wherein the chemical moiety comprises a recognition element capable of binding to the receptor, a property-altering element, and a tethering element between the recognition element and the property-altering element, wherein in the presence of binding between the receptor and the target biological agent the fluorescence emitted by the fluorescer differs from that emitted in the absence of binding between the receptor and the target biological agent;
   determining the fluorescence emitted by the composition after combining the composition with the sample and the chemical moiety; wherein when the recognition element is bound to the receptor, the property-altering element is located sufficiently close to the fluorescer such that the fluorescence emitted by the fluorescer is altered from that emitted when binding between the receptor and the chemical moiety does not occur;

and wherein the difference in fluorescence emitted after combining the composition with the sample and the chemical moiety compared to that emitted in the absence of the sample is indicative of the presence and/or amount of the biological agent.

2. The assay of claim 1, wherein the amount of target biological agent present in said sample is correlated with the difference in fluorescence.

3. The assay of claim 1, wherein the chemical moiety is combined with the composition prior to the sample.

4. The assay of claim 1, wherein the chemical moiety and the sample are simultaneously combined with the composition.

5. The assay of claim 1, wherein the sample is combined with the composition prior to the chemical moiety.

6. The assay of claim 5, wherein the sample and the composition are incubated prior to combining the chemical moiety.

7. The assay of claim 1, wherein the target biological agent is selected from the group consisting of proteins, viruses, bacteria, spores, cells, microorganisms, antibodies, antibody fragments, nucleic acids and toxins.

8. The assay of claim 1, wherein the fluorescer is anchored to the support via adsorption or a covalent linkage.

9. The assay of claim 1, wherein the fluorescer comprises a plurality of fluorescent species associated with one another such that the property-altering element superquenches fluorescence emitted from the fluorescer when the chemical moiety is bound to the receptor.

10. The assay of claim 9, wherein the fluorescer is a fluorescent polymer.

11. The assay of claim 10, wherein the fluorescent polymer is selected from the group consisting of a neutral polymer and a charged polymer.

12. The assay of claim 9, wherein the fluorescer comprises fluorescent species which are covalently or non-covalently linked and aggregate to form a polymer ensemble.

13. The assay of claim 1, wherein the fluorescer and the receptor are each covalently bound to the support.

14. The assay of claim 1, wherein the receptor is covalently bound to the fluorescer.

15. The assay of claim 9, wherein the fluorescer is a conjugated polymer or a J-aggregate of assembled monomers or oligomers.

16. The assay of claim 10, wherein the fluorescent polymer is selected from the group consisting of conjugated polyelectrolytes, functionalized conjugated oligomers, uncharged conjugated polymers, charged conjugated polymers and conjugated polymer blends.

17. The assay of claim 1, wherein the recognition element is selected from the group consisting of chemical ligands, hormones, antibodies, antibody fragments, oligonucleotides, antigens, polypeptides, glycolipids, proteins, protein fragments, enzymes, peptide nucleic acids and polysaccharides.

18. The assay of claim 1, wherein the tethering element is selected from the group consisting of a single bond, a single divalent atom, a divalent chemical moiety, a multivalent chemical moiety, polyethylene, polyethylene oxides, polyamides and non-polymeric organic structures.

19. The assay of claim 1, wherein the property-altering element is selected from the group consisting of methyl viologen, quinones, metal complexes, fluorescent dyes, non-fluorescent dyes, electron accepting moieties, electron donating moieties and energy accepting moieties.

20. The assay of claim 1, wherein the support is selected from the group consisting of streptavidin coated spheres, polymer microspheres, silica microspheres, organic nanoparticles, inorganic nanoparticles, magnetic beads, magnetic particles, semiconductor nanoparticles quantum dots, membranes, slides, plates and test tubes.

* * * * *